(12) United States Patent
Kim et al.

(10) Patent No.: US 10,760,056 B2
(45) Date of Patent: Sep. 1, 2020

(54) THREE-DIMENSIONAL CO-CULTURE METHOD FOR ADIPOCYTES AND MACROPHAGES

(71) Applicant: Korea Research Institute of Chemical Technology, Daejeon (KR)

(72) Inventors: Ki Young Kim, Daejeon (KR); Sung Bum Park, Daejeon (KR); Sang Dal Rhee, Daejeon (KR); Hi Youn Kim, Daejeon (KR); Won Hoon Jung, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 150 days.

(21) Appl. No.: 15/746,628

(22) PCT Filed: Jul. 22, 2016

(86) PCT No.: PCT/KR2016/008020
§ 371 (c)(1),
(2) Date: Jan. 22, 2018

(87) PCT Pub. No.: WO2017/014595
PCT Pub. Date: Jan. 26, 2017

(65) Prior Publication Data
US 2018/0208898 A1  Jul. 26, 2018

(30) Foreign Application Priority Data
Jul. 23, 2015 (KR) .......................... 10-2015-0104272

(51) Int. Cl.
| C12N 5/077 | (2010.01) |
| G01N 33/50 | (2006.01) |
| C12N 5/0786 | (2010.01) |
| G01N 33/68 | (2006.01) |

(52) U.S. Cl.
CPC ......... *C12N 5/0653* (2013.01); *C12N 5/0645* (2013.01); *G01N 33/50* (2013.01); *G01N 33/5044* (2013.01); *G01N 33/6893* (2013.01); *C12N 2502/1157* (2013.01); *C12N 2502/1305* (2013.01); *C12N 2503/04* (2013.01); *C12N 2513/00* (2013.01); *C12N 2533/54* (2013.01); *C12N 2533/74* (2013.01); *G01N 2333/46* (2013.01); *G01N 2800/042* (2013.01)

(58) Field of Classification Search
CPC ............... C12N 5/0653; C12N 5/0645; C12N 2503/04; C12N 2502/1157; C12N 2533/74; C12N 2502/1305; C12N 2513/00; C12N 2533/54; G01N 33/5044; G01N 33/6893; G01N 33/50; G01N 2800/042
See application file for complete search history.

(56) References Cited

U.S. PATENT DOCUMENTS

| 5,032,508 A | 7/1991 | Naughton et al. |
| 9,039,998 B2 | 5/2015 | Guillemot et al. |
| 9,468,657 B2 | 10/2016 | Nakamura et al. |
| 2007/0243574 A1 | 10/2007 | Williams et al. |
| 2009/0221022 A1 | 9/2009 | MacQueen et al. |
| 2014/0099709 A1 | 4/2014 | Presnell et al. |
| 2015/0246072 A1 | 9/2015 | Bhatia et al. |
| 2015/0275172 A1 | 10/2015 | Tabata et al. |

FOREIGN PATENT DOCUMENTS

| CN | 104768586 A | 7/2015 |
| EP | 1782849 A2 | 5/2007 |
| JP | 2010111585 A | 5/2010 |
| JP | 2010178701 A | 8/2010 |
| JP | 2013521033 A | 6/2013 |
| JP | 201473107 A | 4/2014 |
| KR | 1020130119663 A | 11/2013 |
| KR | 1020150020702 A | 2/2015 |
| WO | 9002796 A1 | 3/1990 |
| WO | 2007113591 A2 | 10/2007 |
| WO | 2011155518 A1 | 12/2011 |

OTHER PUBLICATIONS

Gruene et al., Adipogenic differentiation of laser-printed 3D tissue grafts consisting of human adipose-derived stem cells. Biofabrication, vol. 3 (2011) pp. 1-9. (Year: 2011).*
Murphy et al., Evaluation of hydrogels for bio-printing applications. Journal of Biomedical Materials Research, vol. 101A (Jan. 2013) pp. 272-284. (Year: 2013).*
Hirai et al., "Inhibitory effect of naringenin chalcone on inflammatory changes in the interaction between adipocytes and macrophages", Life Sciences, 2007, pp. 1272-1279, vol. 81.
Kim et al., "B-cell-activating factor is a regulator of adipokines and a possible mediator between adipocytes and macrophages", Experimental & Molecular Medicine, 2013, vol. 45, Article No. e4.
Kim et al., "Esculetin inhibits the inflammatory response by inducing heme oxygenase-1 in cocultured macrophages and adipocytes", Food & Function, 2014, pp. 2371-2377, vol. 5.
Kim et al., "Tomato extract suppresses the production of proinflammatory mediators induced by interaction between adipocytes and macrophages", Bioscience, Biotechnology, and Biochemistry, 2015, pp. 82-87, vol. 79, No. 1.
Park et al., "Development of in vitro three-dimensional co-culture system for metabolic syndrome therapeutic agents", Diabetes, Obesity and Metabolism, 2019, pp. 1146-1157, vol. 21, No. 5.

(Continued)

*Primary Examiner* — Kara D Johnson
(74) *Attorney, Agent, or Firm* — The Webb Law Firm

(57) ABSTRACT

Provided herein is a three-dimensional co-culture of adipocytes and macrophages, wherein, in a hydrogel scaffold containing adipocytes and macrophages, the adipocytes and the macrophages are co-cultured to form a fat-like tissue, which can be then utilized in the studies and medicine development for treating metastatic diseases associated with adipose tissue.

3 Claims, 13 Drawing Sheets

Specification includes a Sequence Listing.

(56) References Cited

OTHER PUBLICATIONS

Suganami et al., "A Paracrine Loop Between Adipocytes and Macrophages Aggravates Inflammatory Changes—Role of Free Fatty Acids and Tumor Necrosis Factor α", Arteriosclerosis, Thrombosis, and Vascular Biology, 2005, pp. 2062-2068, vol. 25, No. 10.
Kasai, "Inkjet Technology Applied to Bio-printing", Advanced Marking Research Laboratories Research & Development Management Headquarters, 2011, pp. 251-255, vol. 48, No. 4.
Keophiphath et al., "Macrophage-Secreted Factors Promote a Profibrotic Phenotype in Human Preadipocytes", Molecular Endocrinology, 2009, pp. 11-24, vol. 23, No. 1.
Stanton et al., "Bioprinting of 3D hydrogels", Lab Chip, 2015, pp. 3111-3115, vol. 15.
Xie et al., "Interactive Changes between Macrophages and Adipocytes", Clinical and Vaccine Immunology, 2010, pp. 651-659, vol. 17, No. 4.
Gruene et al., "Adipogenic differentiation of laser-printed 3D tissue grafts consisting of human adipose-derived stem cells", Biofabrication, 2011, 9 pages, vol. 3, No. 1, Article No. 015005.

\* cited by examiner

[FIG. 1]

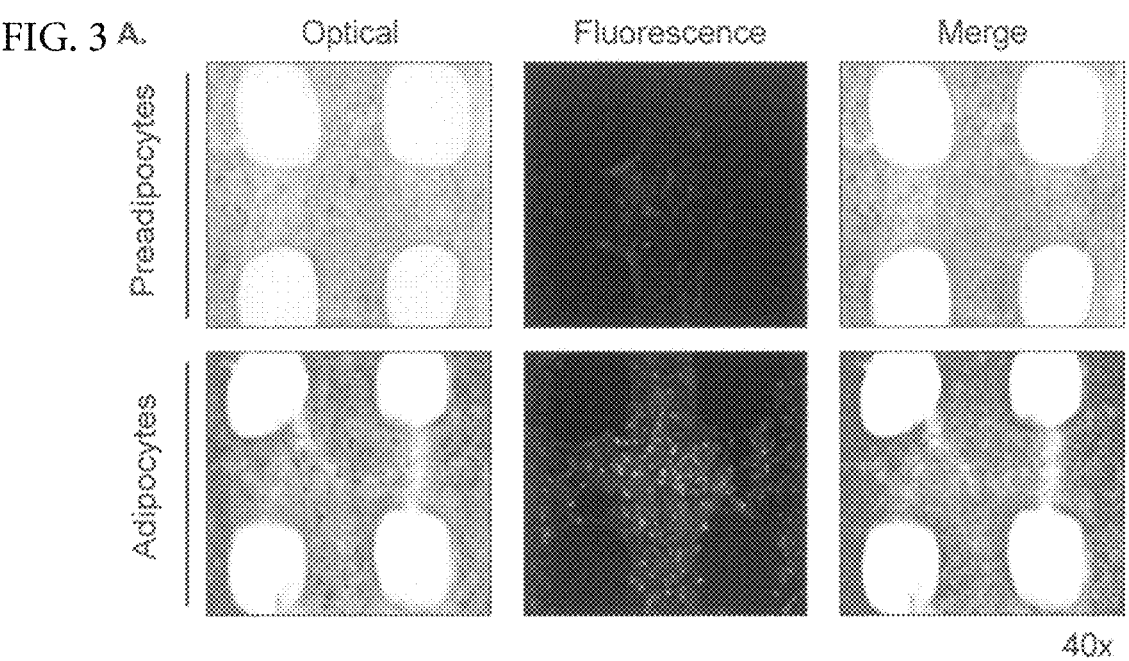

SEQUENCE LISTING

<160> NUMBER OF SEQ ID NOS: 12

<210> SEQ ID NO 1
<211> LENGTH: 20

-continued

```
<212> TYPE: DNA
<213> ORGANISM: Artificial Sequence
<220> FEATURE:
<223> OTHER INFORMATION: PPAR2 Forward Primer

<400> SEQUENCE: 1
ccctggcaaa gcatttgtat                                                   20

<210> SEQ ID NO 2
<211> LENGTH: 20
<212> TYPE: DNA
<213> ORGANISM: Artificial Sequence
<220> FEATURE:
<223> OTHER INFORMATION: PPAR2 Reverse Primer

<400> SEQUENCE: 2
gaaactggca cccttgaaaa                                                   20

<210> SEQ ID NO 3
<211> LENGTH: 20
<212> TYPE: DNA
<213> ORGANISM: Artificial Sequence
<220> FEATURE:
<223> OTHER INFORMATION: G3PD Forward Primer

<400> SEQUENCE: 3
agagatgctc gccacagaat                                                   20

<210> SEQ ID NO 4
<211> LENGTH: 20
<212> TYPE: DNA
<213> ORGANISM: Artificial Sequence
<220> FEATURE:
<223> OTHER INFORMATION: G3PD Reverse Primer

<400> SEQUENCE: 4
aaagggtctc tggggtctgt                                                   20

<210> SEQ ID NO 5
<211> LENGTH: 20
<212> TYPE: DNA
<213> ORGANISM: Artificial Sequence
<220> FEATURE:
<223> OTHER INFORMATION: FABP4 Forward Primer

<400> SEQUENCE: 5
catcagcgta aatggggatt                                                   20

<210> SEQ ID NO 6
<211> LENGTH: 20
<212> TYPE: DNA
<213> ORGANISM: Artificial Sequence
<220> FEATURE:
<223> OTHER INFORMATION: FABP4 Reverse Primer

<400> SEQUENCE: 6
tcgactttcc atcccacttc                                                   20

<210> SEQ ID NO 7
<211> LENGTH: 21
<212> TYPE: DNA
<213> ORGANISM: Artificial Sequence
<220> FEATURE:
<223> OTHER INFORMATION: GLUT4 Forward Primer

<400> SEQUENCE: 7
```

-continued

```
ctccttctat ttgccgtcct c                                              21

<210> SEQ ID NO 8
<211> LENGTH: 21
<212> TYPE: DNA
<213> ORGANISM: Artificial Sequence
<220> FEATURE:
<223> OTHER INFORMATION: GLUT4 Reverse Primer

<400> SEQUENCE: 8
ctgttttgcc cctcagtcat t                                              21

<210> SEQ ID NO 9
<211> LENGTH: 20
<212> TYPE: DNA
<213> ORGANISM: Artificial Sequence
<220> FEATURE:
<223> OTHER INFORMATION: FAS Forward Primer

<400> SEQUENCE: 9
acatggtagc tgccctcaag                                                20

<210> SEQ ID NO 10
<211> LENGTH: 20
<212> TYPE: DNA
<213> ORGANISM: Artificial Sequence
<220> FEATURE:
<223> OTHER INFORMATION: FAS Reverse Primer

<400> SEQUENCE: 10
gcgcagtacc gtagaaggac                                                20

<210> SEQ ID NO 11
<211> LENGTH: 18
<212> TYPE: DNA
<213> ORGANISM: Artificial Sequence
<220> FEATURE:
<223> OTHER INFORMATION: 18SRNA Forward Primer

<400> SEQUENCE: 11
cggttctatt ttgttggt                                                  18

<210> SEQ ID NO 12
<211> LENGTH: 20
<212> TYPE: DNA
<213> ORGANISM: Artificial Sequence
<220> FEATURE:
<223> OTHER INFORMATION: 18SRNA Reverse Primer

<400> SEQUENCE: 12
agtcggcatc gtttatggtc                                                20
```

THREE-DIMENSIONAL CO-CULTURE METHOD FOR ADIPOCYTES AND MACROPHAGES

CROSS-REFERENCE TO RELATED APPLICATIONS

This application is the United States national phase of International Application No. PCT/KR2016/008020 filed Jul. 22, 2016, and claims priority to Korean Patent Application No. 10-2015-0104272 filed Jul. 23, 2015, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1800586_ST25.txt. The size of the text file is 2,650 bytes, and the text file was created on Jan. 17, 2018.

TECHNICAL FIELD

The present invention relates to a three-dimensional co-culture method of adipocytes and macrophages, which is a cell culture method capable of forming a similar structure to three-dimensionally formed bio-adipose tissue.

BACKGROUND ART

In development of a therapeutic agent for metabolic diseases such as obesity, diabetes and arteriosclerosis, there are many difficulties in developing a new medicine, since the drugs which initially showed excellent efficacy in vitro had reduced efficacy in animal experiments in vivo. In order to solve the problem, there is needed a similar in vitro model to an in vivo model, which allows correct efficacy and toxicity to be predicted from the early stages of drug development.

In vivo such as human cells and tissue, growth and differentiation by interaction between cells occur, thereby having a complicated three-dimensional structure. However, the method used for cell or tissue culture in laboratories and the like corresponds to two-dimensional culture, and thus, there are many difficulties in studying the function of in vivo tissue or the reaction actually occurring in tissue.

For studying the reaction of in vivo tissue and the functions thereof, the research using three-dimensional scaffolds is actively proceeding in the fields of tissue engineering or biotechnology, and the research such as a cell differentiation mechanism, disease therapeutic agent development and tissue regeneration is being applied by implanting three-dimensional artificial tissue scaffolds (Korean Patent Laid-Open Publication No. 10-2013-0119663). However, the three-dimensional scaffolds are artificially manufactured, and since the in vivo structure composed of interaction between cells, such as real tissue or organs is so diverse and complicated, there is a technical limitation in forming a similar structure such as tissue.

In order to solve the existing problems and develop a new medicine for metabolic diseases, the present inventors have developed a culture method allowing different cells from each other to represent the similar function to that of adipose tissue through interaction between cells in a three-dimensional environment like in vivo.

DISCLOSURE

Technical Problem

An object of the present invention is to provide a co-culture method of two or more cells, thereby representing the similar function to that of in vivo tissue through interaction between cells, and developing a drug efficacy screening system and a new medicine for basic study of in vivo tissue and metabolic disease treatment therefrom.

Technical Solution

In one general aspect, a three-dimensional co-culture method of adipocytes and macrophages includes: preparing a mixture including uniformly mixed preadipocytes, macrophages and hydrogels for forming an adipose tissue-like structure; manufacturing hydrogel scaffolds including preadipocytes and macrophages, using a three-dimensional cell-printing system; and treating a culture fluid so that the preadipocytes and the macrophages included in the hydrogel scaffolds are proliferated and differentiated to form the adipose tissue-like structure.

The macrophages in the hydrogels may be included at 1 to 10% (w/v) relative to the total number of preadipocytes.

The hydrogels in the mixture including uniformly mixed preadipocytes, macrophages and hydrogels may be alginate hydrogels including alginates, collagen and gelatin.

The alginates in the alginate hydrogels may be included at 2.0 to 4.0% (w/v) relative to the mixture.

In another general aspect, an analysis method of metabolic disease includes: forming a similar structure to adipose tissue by the co-culture method of adipocytes and macrophages, and then investigating any one or more of gene expression and protein activity using the structure to analyze the metabolic disease.

Advantageous Effects

The co-culture method of adipocytes and macrophages according to the present invention may form a structure having a similar function to that of in vivo adipose tissue by interaction between cells of the adipocytes and the macrophages in hydrogel scaffolds. Further, the adipose tissue-like structure formed in the hydrogel scaffolds may represent similar gene expression and protein activity to those of in vivo adipose tissue, thereby being used in research for adipose tissue-related metabolic disease treatment and new medicine development.

BEST MODE

Figure 1:
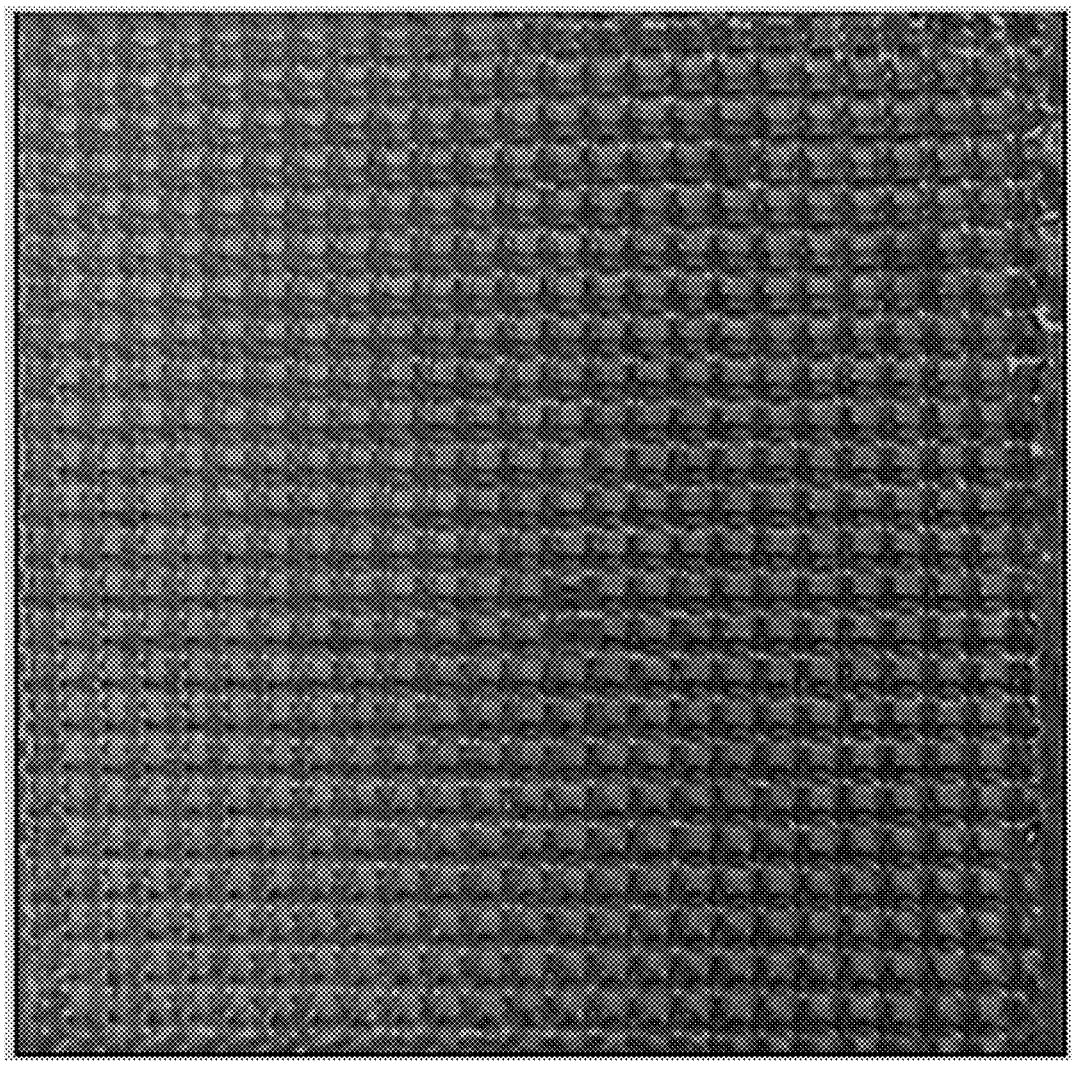
FIG. 1 represents hydrogel scaffolds manufactured by a three-dimensional cell-printing system.

Hereinafter, the present invention will be described in detail. Any known contents which may obscure the subject matter may be omitted from the description and the drawings of the present invention. The terms which are not defined separately for the description of the present invention should be interpreted as having the meaning which may be commonly understood by a person with ordinary skill in the art to which the present invention pertains.

The present invention relates to a three-dimensional co-culture method of adipocytes and macrophages, and a technique therefor.

In the present invention, the co-culture method of adipocytes and macrophages is a three-dimensional co-culture method using adipocytes and macrophages including: preparing a mixture including uniformly mixed preadipocytes, macrophages and hydrogels; manufacturing hydrogel scaffolds including the preadipocytes and the macrophages from the mixture, using a three-dimensional cell-printing system; and treating a culture fluid to proliferate and differentiate the preadipocytes into adipocytes, so that the preadipocytes and the macrophages included in the hydrogel scaffold function similarly to the adipose tissue.

In the co-culture method of the present invention, the preadipocytes, the macrophages, and the concentration or cell density of the macrophages included in the hydrogel mixture may be adjusted for survival, differentiation and proliferation of adipocytes, and forming an adipose tissue-like structure. When the macrophages are present in a trace amount or not present, they hardly have the function of adipose tissue, and as the concentration of the macrophages is increased, a differentiation rate of adipocytes is decreased, thereby causing a decrease in expression of a specific gene which is expressed in adipocytes and may form like adipose tissue, a decrease of protein activity, and the like.

In the mixture of preadipocytes, macrophages and hydrogels for forming hydrogel scaffolds in the present invention, the content of the preadipocytes is $1 \times 10^5$ cells/ml or more, preferably $1 \times 10^5$ cells/ml to $1 \times 10^7$ cells/ml, more preferably $1 \times 10^6$ cells/ml to $1 \times 10^7$ cells/ml. When the preadipocytes are included at less than $1 \times 10^5$ cells/ml, cell proliferation and survival may not be active, or when included at more than $1 \times 10^7$ cells/ml, the cells may fall off to the outside of the scaffolds.

In the mixture of preadipocytes, macrophages and hydrogels for forming hydrogel scaffolds in the present invention, the content of the macrophages is 10% or less, 10 to 5.5%, 5.5 to 4.5%, 4.5 to 3.5%, 3.5 to 2.5%, 2.5 to 1.5%, 1.5 to 0.5%, preferably 2.0 to 1.0%, more preferably 1.2 to 0.8% (w/v), relative to the preadipocytes included in the hydrogel scaffolds. For example, when the preadipocytes are included at $1 \times 10^5$ cells/ml, for the content of the macrophages of 1.0 to 2.0%, the macrophages may be included by adjusting the number to $1 \times 10^3$ cells/ml to $2 \times 10^3$ cells/ml or less.

According to an exemplary embodiment of the present invention, adipogenesis is smoothly done at the content of the macrophages of 1.0 to 2.0% (w/v), relative to the preadipocytes for producing hydrogel scaffolds, and a similar function to that of actual adipose tissue appears, as in the result of increased insulin resistance.

In the present invention, the hydrogels may allow polymer chains to form a network, using a cell culture medium, a culture fluid, or water as a solvent, in which aqueous polymers and the like may chemically form crosslinks, or be physically bonded to each other, thereby forming three-dimensional hydrogel scaffolds. The hydrogel used in the present invention is not significantly limited, and collagen, chitosan, hyaluronic acid, and gelatin may be used, and it is preferred to include alginates derived from preferably algae. In the case of using algae-based hydrogels, it is preferred that the content of alginate is appropriately adjusted to maintain the hydrogel scaffolds to be undissolved, during a preadipogenesis period and the subsequent course of further experiment, in co-culture of adipocytes and macrophages.

In the present invention, the alginate hydrogels refer to hydrogels prepared by including alginates derived from algae. The alginates in the alginate hydrogels are an aqueous polymer electrolyte, and may form crosslinks, using a polyvalent cation salt such as calcium chloride. In the case of the algae-based hydrogels, the alginate content is more than 2.5%, 2 to 4%, 2.5 to 4%, 2.8 to 3.0%, 3 to 4%, 3.5 to 4%, preferably more than 2.5%, equal to or less than 3.0% (w/v), most preferably 3.0% (w/v), relative to a mixture of adipocytes, macrophages and alginate hydrogels for producing hydrogel scaffolds. When the alginate content is insufficient, solubility of the structure is increased, and when the alginate content is high, proliferation and survival rate of cells may be decreased.

According to an exemplary embodiment of the present invention, when the content of alginates derived from brown algae is 2.0% (w/v), survival and proliferation of adipocytes are very active, but the form does not last relatively long in co-culture of adipocytes and macrophages in the hydrogel scaffolds, thereby causing difficulty in culture and application of study. Further, when the alginate content is 2.5% (w/v) and 3.0% (w/v), the hydrogel scaffold form was sufficiently maintained until like adipose tissue was formed, and survival and proliferation of adipocytes are also constantly maintained. In addition, when the alginate content is 3.5% (w/v) or more, persistence of a hydrogel scaffold form is excellent, but survival and proliferation of adipocytes may be decreased.

In the present invention, the hydrogels may further include gelatin and collagen, and it is preferred that the contents of gelatin and collagen are 5.0 to 10.0% (w/v), respectively, relative to the mixture of preadipocytes, macrophages and hydrogels, but not limited thereto.

In the present invention, preadipocytes, macrophages and hydrogels for forming hydrogel scaffolds are uniformly mixed, and then the mixture is processed through a dispenser of a machine for manufacturing hydrogel scaffolds using a three-dimensional cell-printing system.

In the present invention, the three-dimensional cell-printing system is used for producing hydrogel scaffolds having a stereostructure. The three-dimensional cell-printing may be performed by a machine equipped with an x-y-z stage, a dispenser, a syringe nozzle, a compression controller and a computer system. In the present invention, the hydrogel scaffolds manufactured by the three-dimensional cell-printing system have a stereostructure, and allow three-dimensional cell culture, which is distinguished from two-dimensional culture such as commonly performed cell culture in a medium. The structure of hydrogel scaffolds may be appropriately formed by the components and concentration included in the mixture, design by a program, and pressure and a speed in cell-plotting. The scaffold pattern and structure of the hydrogel scaffolds for cell co-culture are not limited, but it is preferred that the scaffold pattern is in an orthogonal direction, and the scaffolds are formed by multilayer cell-plotting.

According to an exemplary embodiment of the present invention, it is preferred that the scaffold pattern is programmed and designed to be in an orthogonal direction, and cell-plotted scaffolds having a thickness of 0.2 to 0.3 mm are formed, and laminated, thereby manufacturing hydrogel scaffolds having a thickness of around 2.0 to 3.0 mm. The thickness is 0.1 to 3.0 mm, 0.4 to 2.5 mm, 0.8 to 2.5 mm, 0.4 to 2.5 mm, 0.8 to 2.5 mm, 1.2 to 2.5 mm, 1.6 to 2.5 mm, 0.4 to 2.0 mm, 0.8 to 2.0 mm, 1.2 to 2.0 mm, preferably 0.2 to 0.3 mm, more preferably 1.6 to 2.0 mm. When the thickness is further increased, the structure of the cell-plotted scaffold layer positioned at the bottom may collapse in formation of the hydrogel scaffolds. When the structure of the hydrogel scaffolds is not maintained constant, the survival rate, and the proliferation and differentiation degrees of cells may be decreased in co-culture. The hydrogel scaffold may be manufactured to have a tetragonal shape having an area of 10 to 30 cm$^2$, 15 to 25 cm$^2$, preferably 20 to 25 cm$^2$.

In the present invention, it is preferred that the number of preadipocytes to be mixed (cell seeded) when manufacturing the hydrogel scaffolds according to cell-plotting is adjusted so that constant proliferation occurs according to the mixture or hydrogel scaffold design.

According to an exemplary embodiment of the present invention, when the number of cells to be mixed with hydrogels is large, a proliferation rate is increased with culture time, and the number of cells to be mixed is preferably $1 \times 10^5$ cells/ml or more, but not limited thereto. However, when the number of cells is less than $1 \times 10^5$ cells/ml, proliferation may not be smoothly done. In the present invention, the hydrogel scaffolds are a place where similar tissue is formed by cell differentiation and proliferation, and interaction between cells in co-culture. When cell culture is done in a general medium such as a flat medium, each cell interacts with each other only in a certain part, a proliferation direction is one-sided, and even in the case that the number of cells is increased by differentiation and proliferation, cells capable of interacting with each other are limited. In addition, various metabolites secreted from cells are accumulated, and an unbalanced concentration gradient is formed. Thus, in the case of two-dimensional in vitro cell culture, interaction between cells may not be induced to be interaction like in vivo, and it is also difficult to form an in vivo-like structure.

However, in the case of the hydrogel scaffolds according to the present invention, the adipocytes and macrophages are included in the hydrogel scaffolds having a stereostructure, and thus, each cell may interact with each other in all directions around like the cells in vivo, the proliferation direction is not one-sided, and even in the case that the number of cells is increased by differentiation and proliferation, each cell may constantly interact with each other around. In addition, various metabolites secreted in cells are not accumulated in a certain area, and may be secreted in all directions around like in vivo, thereby preventing a non-uniform concentration gradient. By these characteristics, interaction between cells like that in vivo may be induced in co-culture of adipocytes and macrophages, and accordingly, like adipose tissue having a similar function to that of in vivo adipose tissue may be formed.

According to an exemplary embodiment of the present invention, there was a significant difference in gene expression and protein activity in the in vivo adipose tissue between the case of culturing preadipocytes and adipocytes in a general medium, and the case of co-culturing adipocytes and macrophages in hydrogel scaffolds, the like adipose tissue formed by co-culture of adipocytes and macrophages in hydrogel scaffolds represented similar gene expression and protein activity to those of increased adipose differentiation factors and increased insulin resistance in the in vivo adipose tissue in C57BL/6-DIO and C57BL/6Job/ob mice widely known as a model of obesity and diabetes.

According to the present invention, after manufacturing hydrogel scaffolds, the cells included in the hydrogel scaffolds are proliferated and differentiated so that the cells form similar tissue by interaction between the cells. The proliferation and differentiation of the cells included in the hydrogel scaffolds occur by treating a culture fluid for proliferation or differentiation in the hydrogel scaffolds to be absorbed therein. The culture fluid absorbed by a porous stereostructure of the hydrogel scaffolds may be uniformly treated in each cell.

The preadipocytes and the macrophages included in the hydrogel scaffolds are differentiated and proliferated by culture fluid treatment, and the adipocytes and macrophages have a similar function to that of adipose tissue by interaction between cells.

According to the present invention, the adipocytes and the macrophages which are three-dimensionally co-cultured form an adipose tissue-like structure, and it may be recognized from difference in an expression degree of protein related to adipogenesis and insulin resistance in the structure, and a glucose uptake test, whether the like adipose tissue is formed.

According to an exemplary embodiment of the present invention, the like adipose tissue formed according to adipocyte and macrophage co-culture in the hydrogel scaffolds has increased expression of marker protein related to adipogenesis such as FABP4, FAS, ACC and PPARγ2, and decreased expression and activity degree of marker protein related to insulin resistance such as AkT phosphorylation and GLUT4. However, when the preadipocytes or adipocytes are cultured alone, respectively in the hydrogel scaffolds, expression of both marker proteins related to adipogenesis and insulin resistance is increased.

EXAMPLE

Hereinafter, preferred Examples for carrying out the present invention will be described in detail. The present invention is neither limited to the following Examples, nor construed as limited by the Examples.

Example 1

An adipose-like structure was formed by co-culturing adipocytes and macrophages in the following manner:

Culture and Preparation of Preadipocytes and Macrophages

3T3-L1 (# CL-173, ATCC) as preadipocytes and RAW264.7 (# TIB-71, ATCC) as macrophages were prepared, and the cells were cultured in an incubator for culture under a condition of 37° C. and 5% $CO_2$, using a Dulbecco's modified Eagle's medium (Gibco) containing a 1% mixture of 10% fetal bovine serum (Invitrogen, Carsbad, Calif., USA), 100 μg/ml of penicillin, and 100 μg/ml of streptomycin (Invitrogen). After culturing, the cells were washed with DPBS (Dulbecco's Phosphate-Buffered Saline, Gibco), 2 ml of 0.2% trypsin-EDTA (ethylenediaminetetraacetic acid) (Invitrogen) was added thereto, and culture was performed in an incubator at 37° C. and 5% $CO_2$ for 1 minute. Next, cell suspension was centrifuged at 1,500 rpm for 2 minutes, thereby obtaining cell pellets, which were used in the experiment.

Preparation of Mixture Including Preadipocytes, Macrophages and Alginate Hydrogels for Manufacturing Hydrogel Scaffolds 500 ul of gelatin (Sigma-Aldrich), 500 ul of collagen (Sigma-Aldrich), $1 \times 10^7$ preadipocytes and $1 \times 10^5$ macrophages were uniformly mixed, and then the volume was adjusted finally to 9.7 ml with a Dulbecco's modified Eagle's medium. 3 mg of sodium alginate (Sigma-Aldrich) was added to the mixture and rapidly stirred, thereby preparing a mixture for manufacturing 3% alginate hydrogel scaffolds, which were transferred to a dispenser composed of 200-300 μm sized nozzles for manufacturing three-dimensional scaffolds. For active cell-printing, centrifugation at 1000 rpm for 10 seconds was performed to prepare the manufacture of hydrogel scaffolds.

In the same manner as in the above method of preparing the mixture, the amounts of gelatin and collagen were equalized, and the mixture including preadipocytes, macrophages and sodium alginate at different contents from each other was prepared using a Dulbecco's modified Eagle's medium. The content of alginate was adjusted to 2, 2.5, 3.0, 3.5 and 4.0%, respectively, so that the hydrogel scaffolds having different concentrations from each other were manufactured. Further, the seeding density of adipocytes was calculated by a disposable blood counting chamber (hemocytometer-based cell counter, SKC Co. Ltd., Seoul, Korea), so that hydrogel scaffolds including different adipocytes from each other may be manufactured with different number of cells of $1 \times 10^4$, $5 \times 10^4$, $1 \times 10^5$, $4 \times 10^5$, $8 \times 10^5$ and $1 \times 10^6$ cells/ml, respectively. The macrophages were adjusted to 1, 2, 3, 4, 5 and 10% (w/v), respectively, relative to adipocytes and the change in a macrophage concentration in co-culture of the adipocytes and the macrophages was observed.

The hydrogel scaffolds manufactured by the dispenser were reacted with 5% aqueous calcium chloride solution which was rapidly prepared in advance. Here, the scaffolds form crosslinks by calcium chloride treatment.

Manufacture of Hydrogel Scaffolds Using Three-Dimensional Cell-Printing System

The manufacture of hydrogel scaffolds using a three-dimensional (3D) cell-printing system employs a machine equipped with an x-y-z stage, a dispenser, a syringe nozzle, a compression controller, and a computer system (3D Bio-Scaffold Plotting system, PROTek). The dispenser was a storage tank for holding hydrogels, and the computer system adjusted pressure, a feeding speed, a strand size, and a scaffold shape. The cell-plotting system speed, and the pressure were adjusted to 150 mm/s and 650 kPa, respectively. As constant pressure is applied to the dispenser, cell-plotted scaffolds as a three-dimensional scaffold form of a mixture of adipocytes, macrophages and hydrogels were manufactured by plotting on the x-y-z stage layer-by-layer. The manufactured scaffold pattern was designed to be in an orthogonal direction, and the cell-plotted scaffolds in a tetragonal (5×5 cm) shape were laminated to the thicknesses of 0.4, 0.8, 1.2, 1.6 and 2 mm, respectively, thereby manufacturing hydrogel scaffolds including preadipocytes and macrophages.

For the manufactured hydrogel scaffolds, proliferation and stabilization of cells were derived in 100 μg/ml of penicillin, 100 μg/ml of streptomycin (Invitrogen), and a Dulbecco's modified Eagle's medium containing 10% fetal bovine serum for 1 day, and thereafter, differentiation was derived by replacing the medium with dexamethasone, isobutylmethylxanthine, and an insulin-treated Dulbecco's modified Eagle's medium containing 10% fetal bovine serum. After 2 or 3 days of differentiation derivation, the medium was replaced with an insulin-treated Dulbecco's modified Eagle's medium containing 10% fetal bovine serum, and after 2 days of insulin treatment, culture was performed for the purpose of the experiment from day 1 to day 20 in the Dulbecco's modified Eagle's medium containing 10% fetal bovine serum, and analysis for cell survival, proliferation and differentiation was performed. The culture medium was replaced once every two days at most.

Cell Survival and Proliferation Analysis

The cell survival in the hydrogel scaffolds was confirmed using a Live/Dead cell analysis kit (Live/Dead cell assay kit, invitrogen), and a fluorescence microscope (TE2000-U, Nikon). The hydrogel scaffolds were washed with PBS, and stained with calcein and EthD-1 (ethidium homodimer) for 15 minutes in PBS. After staining, the hydrogel scaffolds were washed twice, and green fluorescence (living cells, 495-515 nm) and red fluorescence (dead cells, 495-635 nm) were observed with the fluorescence microscope. For the cell proliferation, a cell counting kit (Cell Counting Kit-8 (CCK-8), Dojindo Laboratories) was used. The hydrogel scaffolds were treated with a 1 ml of medium containing 100 μl of CCK-8 in a 24-well plate, and cultured at 37° C. for 4 hours, and then absorbance at 450 nm was measured with a micro-plate spectrophotometer (BIORAD Inc.).

3T3-LI cell proliferation and survival were most active when alginate was at 2%, but when alginate was at 2%, the hydrogel scaffold structure was deformed or collapsed after about 2 weeks, so that the form was not maintained. When alginate was at 2.5%, cell proliferation and survival were active, but the hydrogel scaffold structure was deformed or collapsed likewise after 3 weeks, so that the form was not maintained. When alginate was at 3%, cell proliferation and survival were active, and the hydrogel scaffold structure was maintained even for a long period of 4 weeks or longer. When alginate was at 3.5% or more, the hydrogel scaffold structure was maintained for a long period, but cell proliferation and survival were decreased to the extent of being visually confirmed (B and C in FIG. 2).

Figure 2:
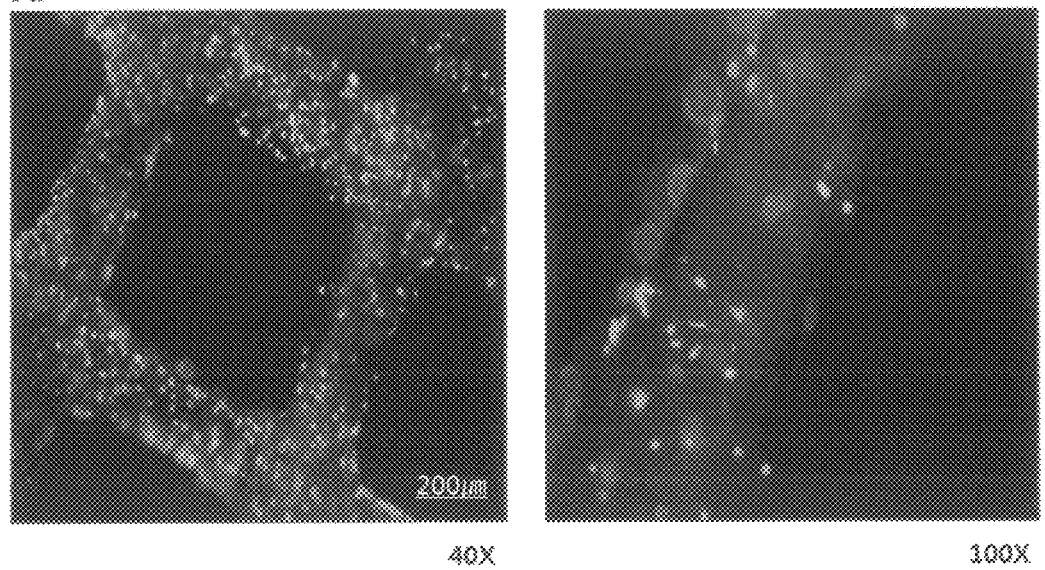
FIGS. 2A-2E represent proliferation and cell survival of 3T3-L1 preadipocytes in hydrogel scaffolds, in which (A) shows an fluorescent image where green fluorescence represents living cells, and red fluorescence represents dead cells; (B) is a graph representing a proliferation degree of cells, when forming a structure by mixing 3T3-L1 preadipocytes having a concentration of 1×105 cells/ml with alginates having different concentrations from each other; (C) is a fluorescent image representing a proliferation degree of cells, when forming a structure by mixing 3T3-L1 preadipocytes having a concentration of 1×105 cells/ml with alginates having different concentrations from each other; (D) is a graph representing cell proliferation, when forming a structure with the different number of 3T3-L1 preadipocytes in 3% (w/v) alginate scaffolds; and (E) is a graph representing 3T3-L1 preadipocyte proliferation depending on a scaffold height, and the results are expressed as average±standard error (S.E.M) according to repetitive experiments (# P<0.05, ## P<0.01, ### P<0.001, compared to the first day).
Figure 2:
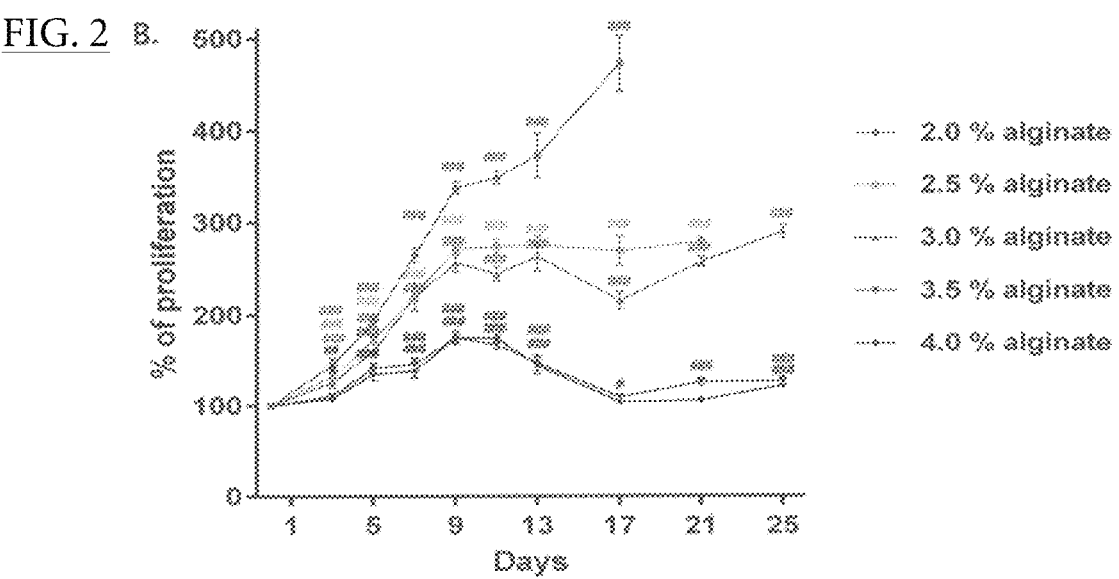
Figure 2:
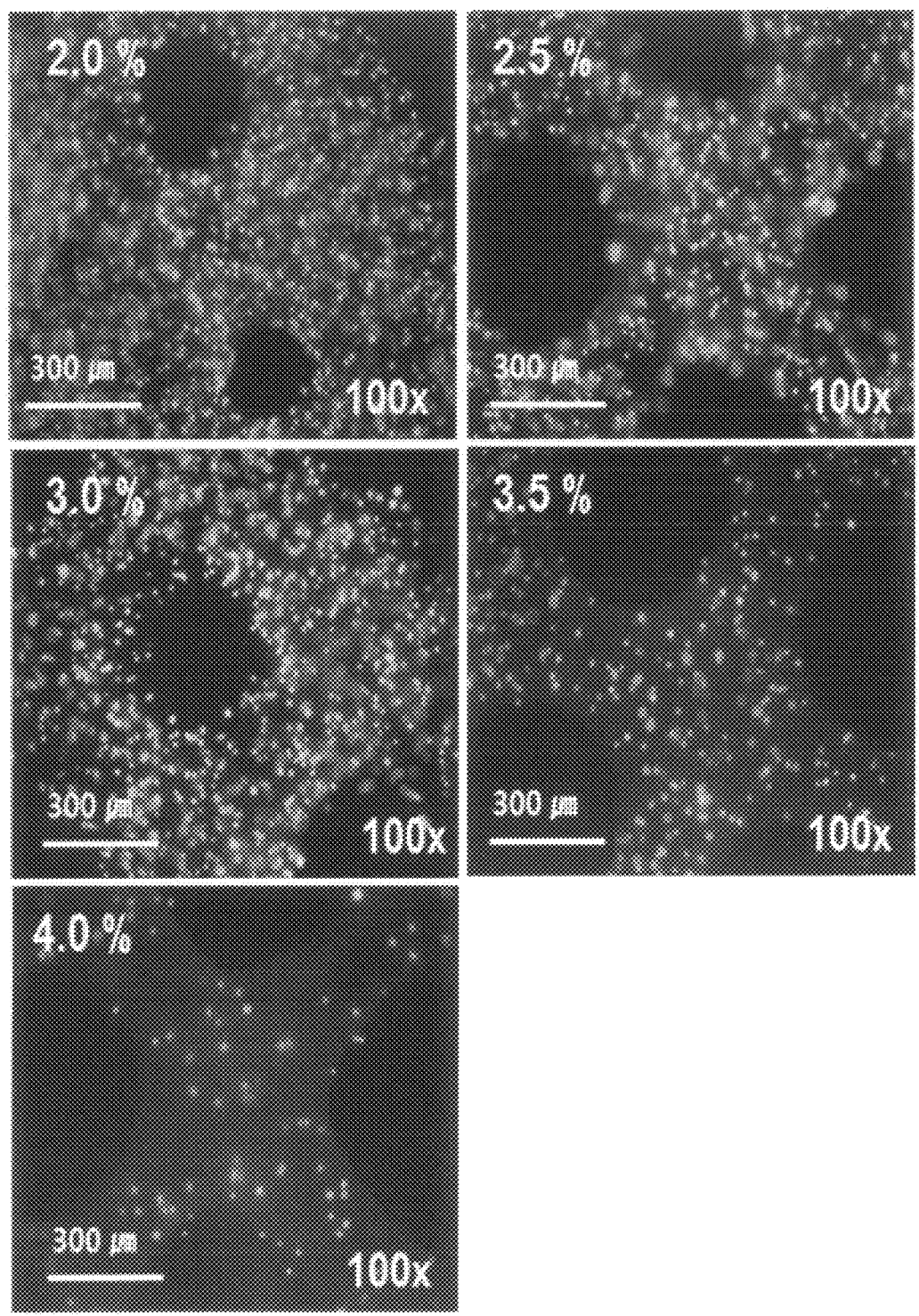
Figure 2:
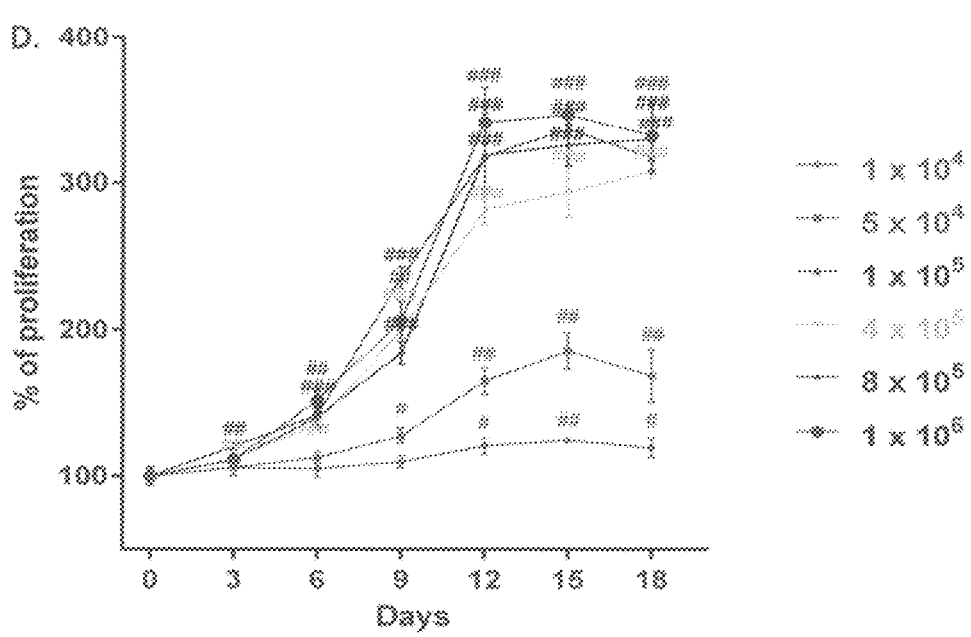
Figure 2:
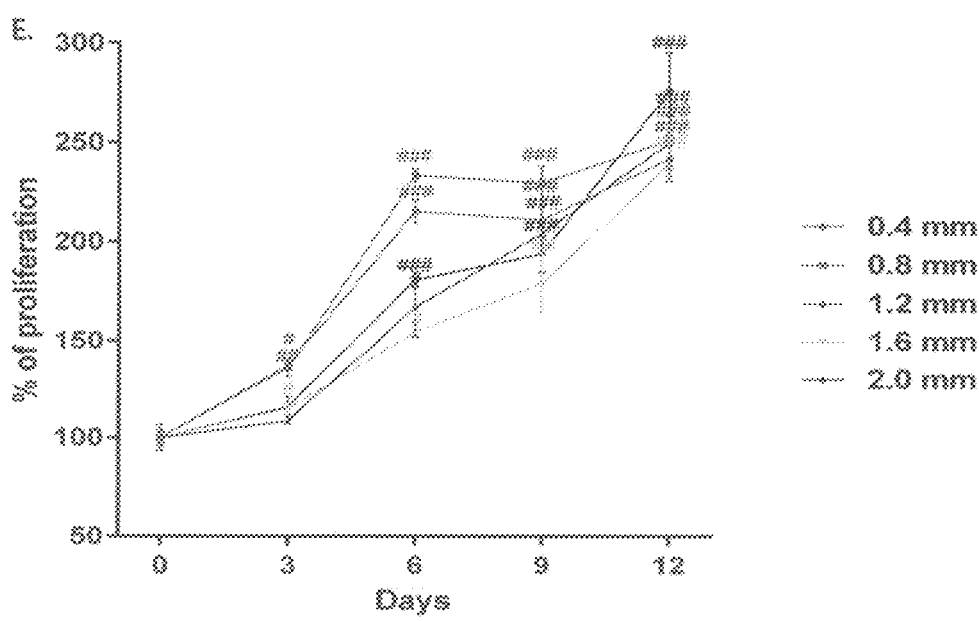

When the number of 3T3-L1 cells is less than $1 \times 10^5$ cells/ml, proliferation did not smoothly occur (D in FIG. 2). Further, when the height of the hydrogel scaffold was 2.0 mm, the proliferation rate was the highest, and when the height was more than 3.0 mm, the substructure of the hydrogel scaffolds was deformed or collapsed between 2-3 weeks, so that the form was not maintained.

Adipocyte and Macrophage Differentiation in Manufactured Scaffolds

The hydrogel scaffolds were differentiated for 3 days using a differentiation derivation medium containing 20 μg/ml of insulin, 0.5 mM isobutylmethylxanthine, and 1 μM dexamethasone, and then allowed to stand for 2 days with the medium replaced with a medium containing 20 μg/ml of insulin, and thereafter, the cells were cultured for 1 day in a general medium (maintained medium).

After culture, adipose particles of adipocytes aged with BODIPY (boron-dipyrromethene) (BODIPY 493/503, Invitrogen) were stained. After staining, they were washed twice with PBS, and as a result of observing the stained adipose particles with a fluorescence microscope, it was confirmed that the stained adipose particles were evenly distributed (A and B in FIG. 3).

Figure 3:
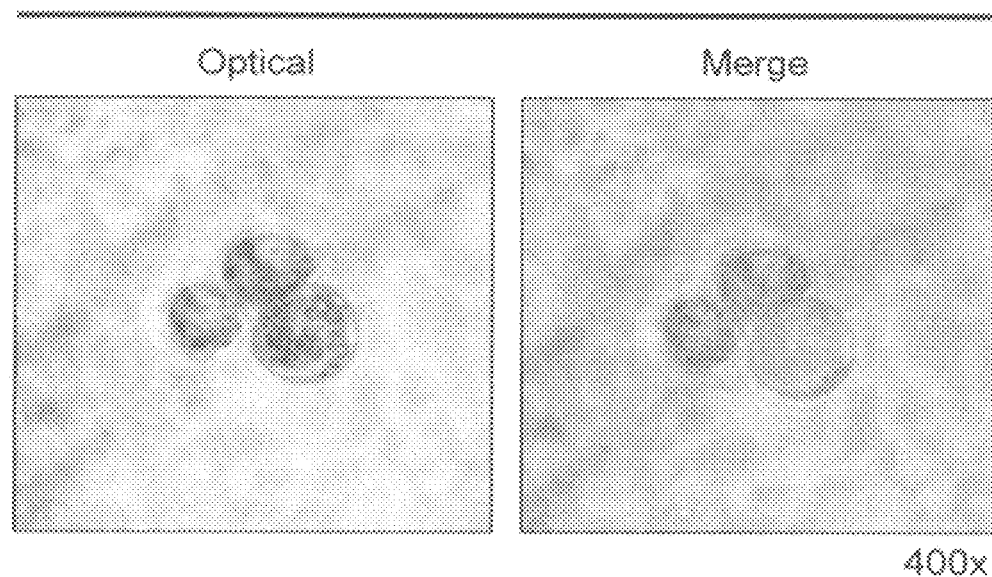
In FIGS. 3A-3E, (A) and (B) represent 3T3-L1 preadipogenesis in hydrogels as fluorescent images using BODIPY (boron-dipyrromethene), which compare 3T3-L1 adipocytes differentiated from the hydrogels having a 3% alginate concentration; (C) compares difference in G6PD enzyme activity between 3T3-L1 preadipocytes and 3T3-L1 adipocytes; (D) represents change in representative genes related to adipogenesis and insulin resistance; and (E) represents difference in expression of representative protein related to adipogenesis and insulin resistance, and the results are expressed as average±standard error (S.E.M) according to repetitive experiments (# P<0.05, ## P<0.01, ### P<0.001, compared to preadipocyte group).
Figure 3:
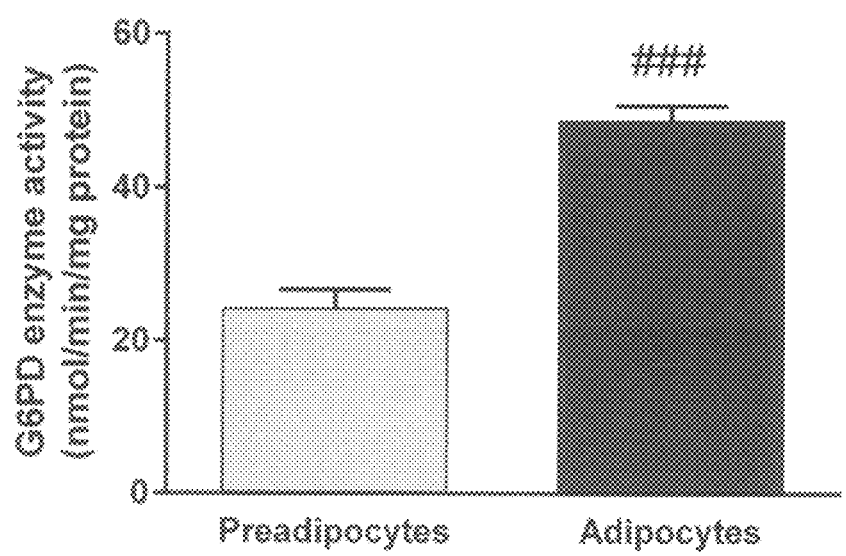
Figure 3:
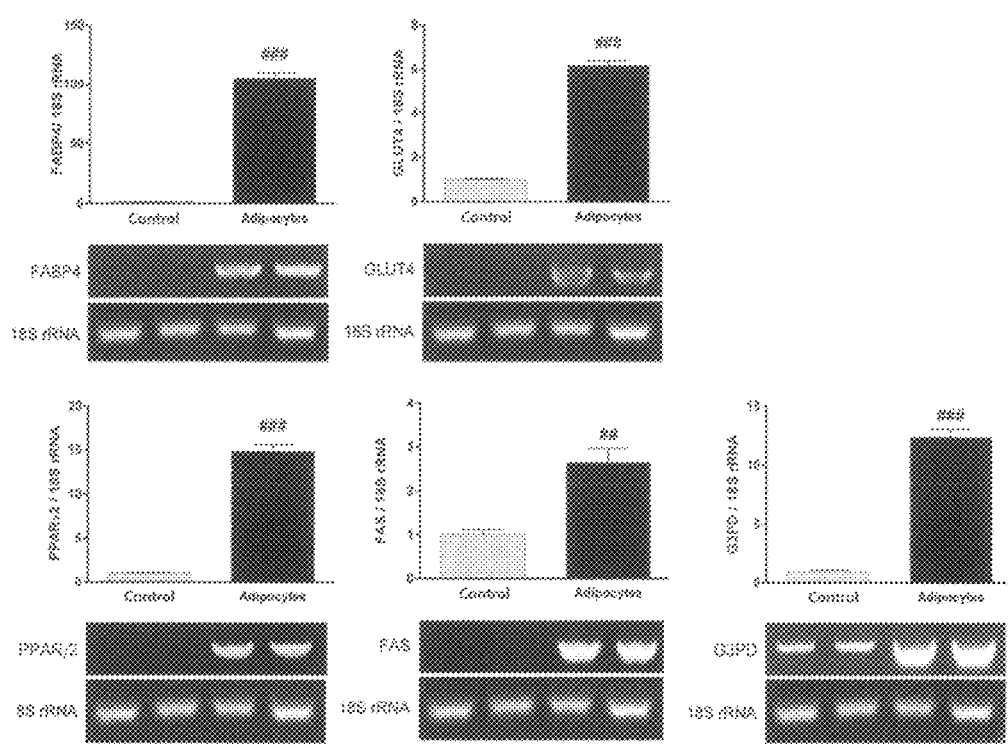
Figure 3:
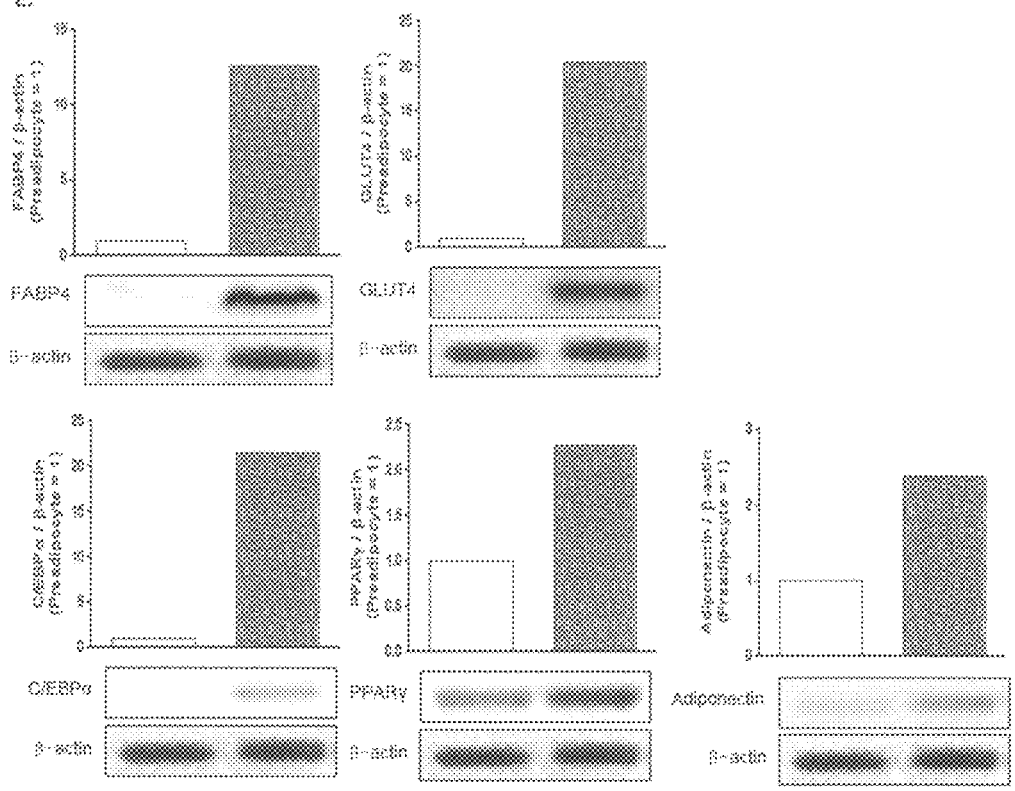

After culture, G6PD enzyme activity in the hydrogel scaffolds was measured with a G6PD analysis kit (Glucose 6 Phosphate Dehydrogenase Assay Kit, abcam), thereby confirming the G6PD enzyme activity which is activated in differentiated adipocytes (C in FIG. 3).

In addition, RNA was separated from cells in the hydrogel scaffolds using trizol (Tri-reagent) (TRIzol, Invitrogen), 2 μg of RNA was reverse-transcribed, and then a gene expression degree and protein activity were confirmed by Real-Time PCR of mRNA, and Western blot assay, respectively. AccuPower RT PreMix (Bioneer Inc., Korea) was used for the reverse transcription, Primer 3 software (http://bioinfo.u-t.ee/primer3/) was used for all primer designs, and the 5'- to 3'-sequences thereof are represented in Table 1.

As a result of confirming the gene expression degree and protein activity, it was recognized that PPARγ2, CEBP/α FABP4, FAS, G3PD and GLUT4 which are adipogenesis process-related transcription factors and adipocyte-related markers were significantly increased (D and E in FIG. 3).

TABLE 1

| Gene | Forward | Reverse |
| --- | --- | --- |
| PPARγ2 | ccctggcaaagcatttgtat (SEQ ID NO: 1) | gaaactggcacccttgaaaa (SEQ ID NO: 2) |
| G3PD | agagatgctcgccacagaat (SEQ ID NO: 3) | aaagggtctctggggtctgt (SEQ ID NO: 4) |
| FABP4 | catcagcgtaaatggggatt (SEQ ID NO: 5) | tcgactttccatcccacttc (SEQ ID NO: 6) |
| GLUT4 | ctccttctatttgccgtcctc (SEQ ID NO: 7) | ctgttttgcccctcagtcatt (SEQ ID NO: 8) |
| FAS | acatggtagctgccctcaag (SEQ ID NO: 9) | gcgcagtaccgtagaaggac (SEQ ID NO: 10) |
| 18S rRNA | cggttctattttgttggt (SEQ ID NO: 11) | agtcggcatcgtttatggtc (SEQ ID NO: 12) |

Figure 4:
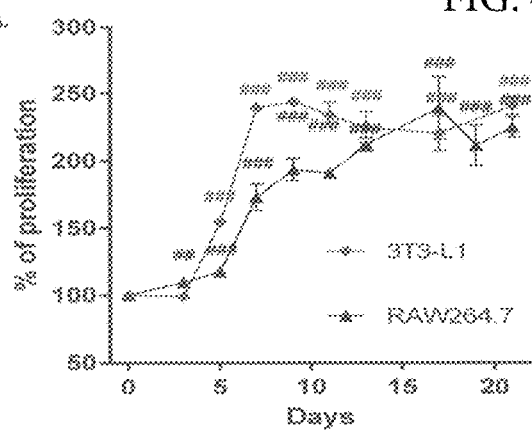
In FIGS. 4A-4I, (A) represents comparison of macrophage cell proliferation in hydrogel scaffolds having a 3% (w/v) alginate concentration with preadipocytes; (B) is a fluorescent image representing a macrophage survival degree in hydrogel scaffolds having a 3% (w/v) alginate concentration; (C) compares difference in expression of representative protein related to adipogenesis and insulin resistance in co-culture mixed with macrophages having a 10% (w/v) concentration of the number of preadipocytes; (D)-(F) compare difference in an adipogenesis degree, and expression of representative protein related to adipogenesis and insulin resistance in co-culture, when the macrophage concentration was different; and (G)-(I) show fluorescent images for the difference in expression of protein related to adipogenesis and insulin resistance, and an adipogenesis degree, when further subdividing the macrophage concentration.
Figure 4:
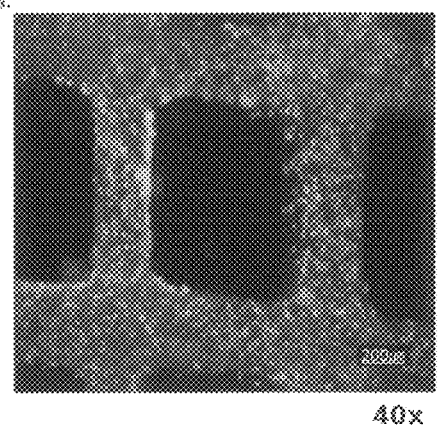
Figure 4:
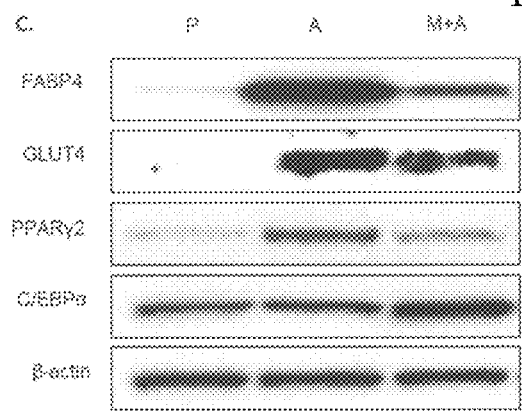
Figure 4:
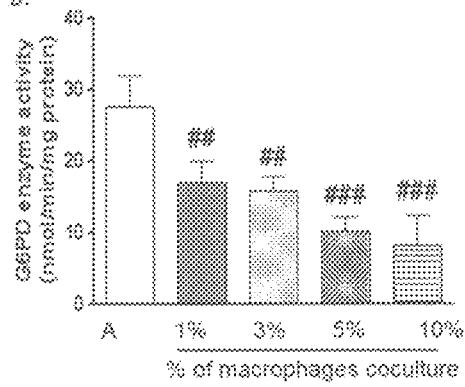
Figure 4:
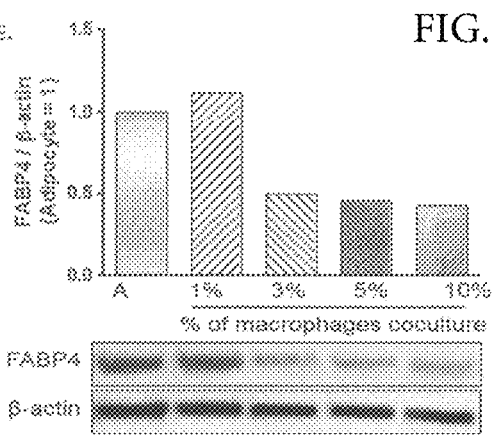
Figure 4:
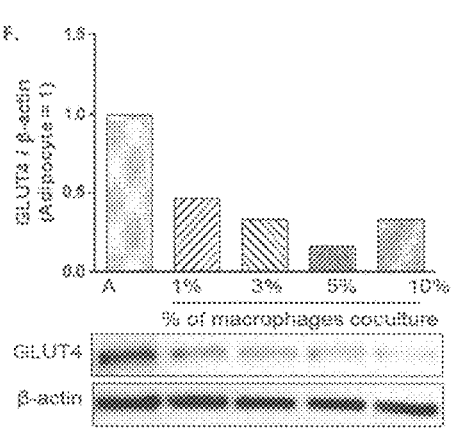
Figure 4:
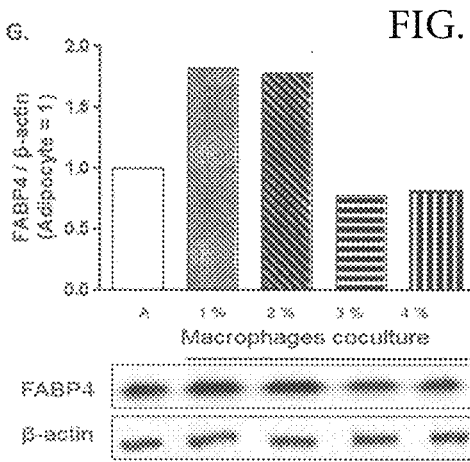
Figure 4:
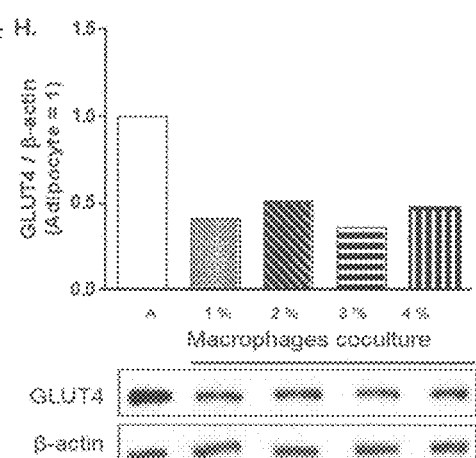
Figure 4:
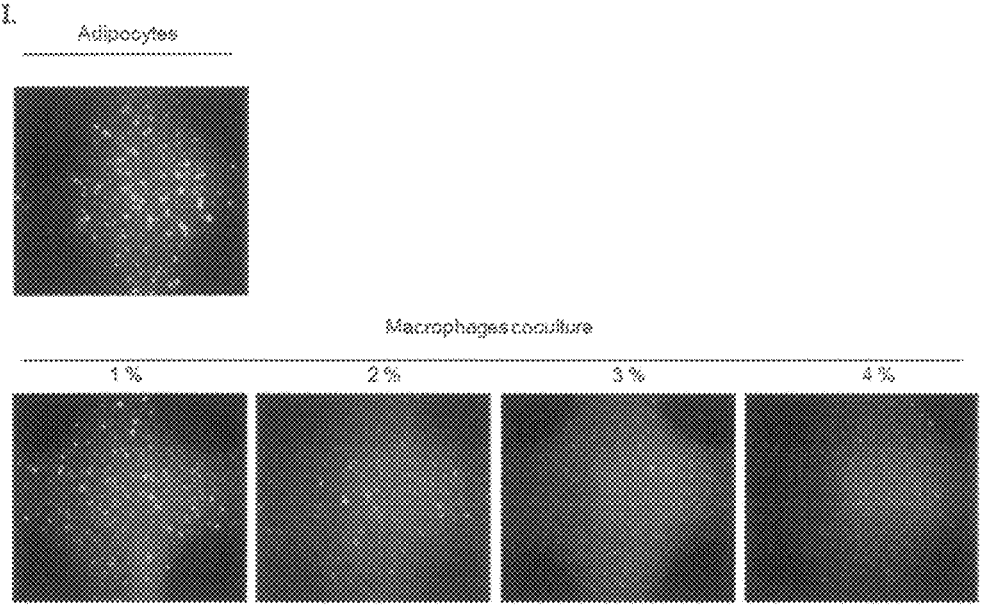

Confirmation of Adipose Tissue-Like Structure Formation by Co-Culture with Macrophages First, 3T3-L1 survival, proliferation and differentiation potency depending on the concentration of macrophage in co-culture were confirmed. The expression of FABP4, GLUT4 and PPARγ was decreased by about 10% in co-culture with macrophages. Further, as the macrophage concentration is increased, it was confirmed that the expression of FABP4 and GLUT4, and the G6PD activity degree were decreased, and when adipocytes and macrophages were co-cultured, it was confirmed that at a macrophage concentration of 2%, FABP4 was increased, but GLUT4 was decreased, and at the macrophage concentration of 3%, the FABP4 activity was rapidly decreased, and the differentiation of preadipocytes to adipocytes was rapidly decreased (G to I in FIG. 4).

Figure 5:
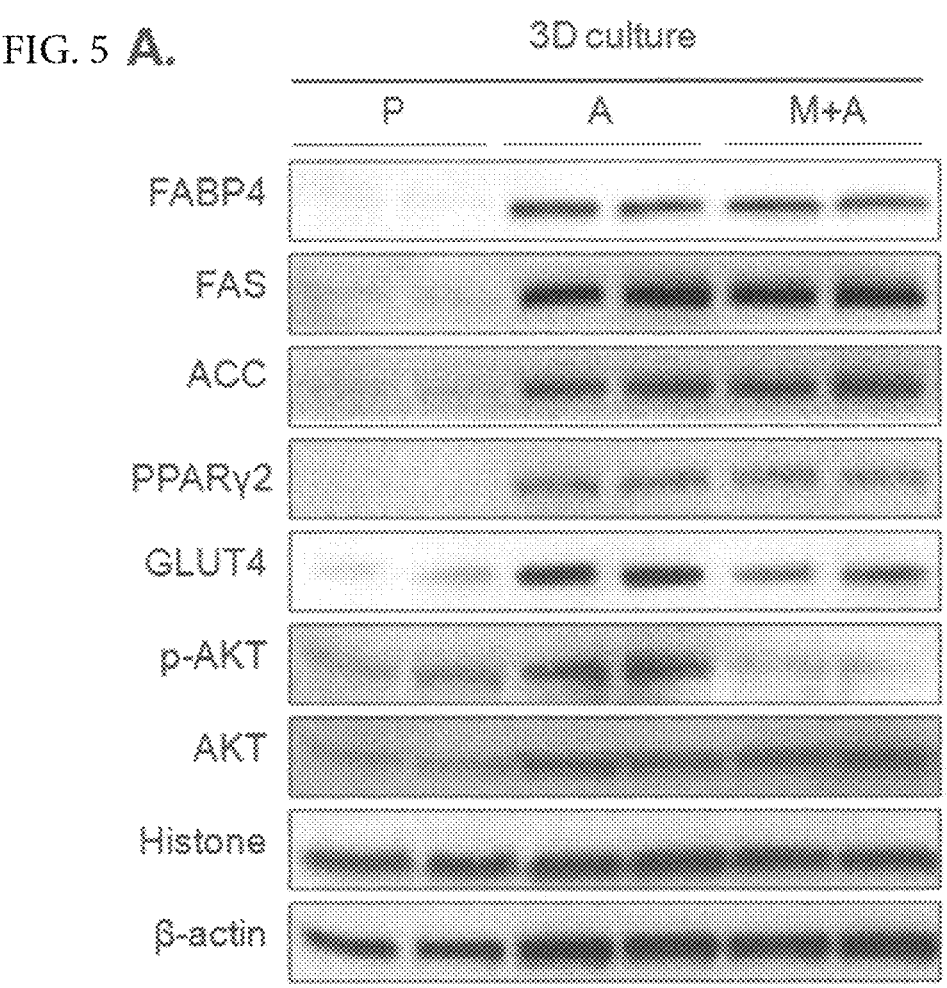
In FIGS. 5A and 5B, (A) represents change in expression of protein related to adipogenesis and insulin resistance in three-dimensional cell co-culture scaffolds; and (B) shows change in insulin resistance in three-dimensional cell co-culture scaffolds through a glucose uptake test.
Figure 5:
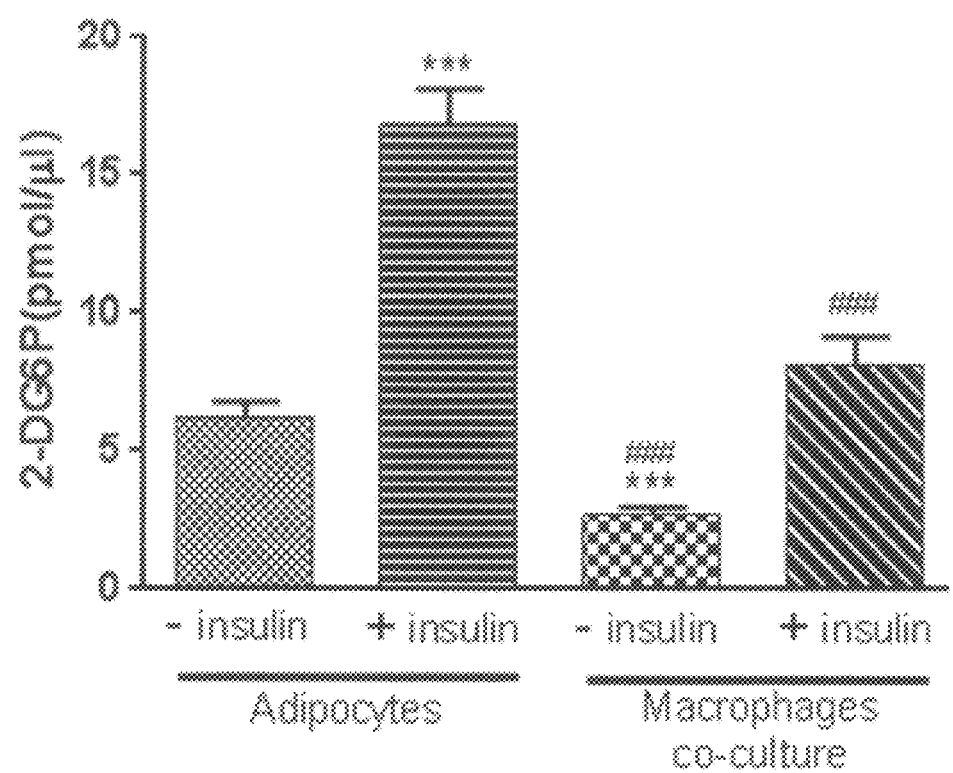

In the three-dimensional single culture and differentiation of preadipocytes, the expression of ACC, FAS and FABP4 related to obesity was increased, and the phosphorylation of AKT and the expression of GLUTA4 related to insulin resistance were increased (A in FIG. 5); there is no difference in the expression of ACC, FAS and FABP4 related to obesity between the three-dimensionally co-cultured and differentiated scaffolds of preadipocytes and macrophages, and the three-dimensionally single-cultured and differentiated scaffolds, thereby confirming that differentiation into adipocytes was smoothly performed (A in FIG. 5); and the phosphorylation of AKT and the expression of GLUT4 related to insulin resistance were decreased, thereby confirming at the protein level that insulin resistance is derived by microphage co-culture. These results are significantly different from the generally known results that the insulin resistance was not increased by an increase of the lipogenesis-related factors such as ACC, FAS and FABP4, phosphorylation of AKT related to insulin resistance, and an increase of the factors such as GLUT4 together, in the two-dimensional single-culture and differentiation of pre-adipocytes. As the results of the glucose uptake test using a glucose uptake evaluation test kit (abcam, UK) (B in FIG. 5) also, it was confirmed that the adipocytes in the scaffolds co-cultured with macrophages had increased insulin resistance due to a significant decrease, despite supply of insulin at a high concentration (1 μg/ml) as compared with the scaffolds with single-cultured adipocytes.

The invention claimed is:

1. A method of co-culturing, comprising:
   (a) preparing a mixture including preadipocytes, macrophages and hydrogels;
   (b) manufacturing hydrogel scaffolds from the mixture using a three-dimensional cell-printing system;
   (c) forming crosslinks using a calcium chloride in the hydrogel scaffolds;
   (d) treating the hydrogel scaffolds of step (c) with a culture fluid; and
   (e) culturing the treated hydrogel scaffolds of step (d) such that the preadipocytes and the macrophages included in the hydrogel scaffolds are proliferated and differentiated to form an adipose-like tissue,
   wherein the hydrogels are alginate hydrogels, and further include one or two or more selected from the group consisting of collagen, chitosan, hyaluronic acid, and gelatin,
   wherein the content of the alginate is greater than 2.5 and less than 3.5% (w/v) relative to the mixture of step (a), and
   wherein the macrophages of step (a) are included at 1.0% to 2.0% relative to the total number of preadipocytes, such that adipogenesis occurs and insulin resistance is increased.

2. The method of claim 1, wherein the alginate hydrogels contain alginates, collagen and gelatin.

3. A method of analyzing activity of adipose-like tissue, comprising:
  (a) preparing a mixture including preadipocytes, macrophages and hydrogels;
  (b) manufacturing hydrogel scaffolds from the mixture of step (a) using a three-dimensional cell-printing system;
  (c) forming crosslinks using a calcium chloride in the hydrogel scaffolds;
  (d) treating the hydrogel scaffolds of step (c) with a culture fluid;
  (e) culturing the treated hydrogel of step (d) such that the preadipocytes and the macrophages included in the hydrogel scaffolds are proliferated and differentiated to compose adipose-like tissue; and
  (f) determining one or more of gene expression and protein activity in the adipose-like tissue of step (e),
  wherein the hydrogels are alginate hydrogels, and further include one or two or more selected from the group consisting of collagen, chitosan, hyaluronic acid, and gelatin,
  wherein the content of the alginate is greater than 2.5 and less than 3.5% (w/v) relative to the mixture of step (a), and
  wherein the macrophages of step (a) are included at 1.0% to 2.0% relative to the total number of preadipocytes, such that adipogenesis occurs and insulin resistance is increased.

* * * * *